United States Patent [19]

Reinhard et al.

[11] Patent Number: 4,658,831
[45] Date of Patent: Apr. 21, 1987

[54] TELEMETRY SYSTEM AND METHOD FOR TRANSMISSION OF ECG SIGNALS WITH HEART PACER SIGNALS AND LOOSE LEAD DETECTION

[75] Inventors: Clyde J. Reinhard, La Habra Heights; Keith A. Fowler, Santa Ana, both of Calif.

[73] Assignee: Pacific Communications, Inc., Santa Ana, Calif.

[21] Appl. No.: 621,722

[22] Filed: Jun. 18, 1984

[51] Int. Cl.⁴ .............................................. A61B 5/04
[52] U.S. Cl. .............................. 128/697; 128/419 PT; 128/903
[58] Field of Search ............... 128/695, 696, 697, 731, 128/903, 419 PT

[56] References Cited

U.S. PATENT DOCUMENTS

| | | | |
|---|---|---|---|
| 3,602,215 | 8/1971 | Parnell | 128/696 |
| 3,859,988 | 1/1975 | Lencioni, Jr. | 128/731 |
| 4,151,513 | 4/1979 | Menken et al. | 128/697 |

OTHER PUBLICATIONS

Briskman, "Electronics", Sep. 6, 1963, pp. 31–37.

*Primary Examiner*—William E. Kamm
*Attorney, Agent, or Firm*—George F. Bethel; Patience K. Bethel

[57] ABSTRACT

The invention is a telemetric biomedical system for simultaneously transmitting a pacer pulse together with lower frequency ECG wave forms and a loose lead signal. The loose lead signal is a low frequency signal applied across the skin electrodes which are attached to a patient subject to cardiac monitoring. In the event that such electrodes should become detached or poorly coupled to the patient, the loose lead signal tends to become open circuited across the leads and can be detected. The loose lead signal and ECG wave form since from the patient, is transmitted in an FM/FM modulated signal, while the pacer pulse is separated from the ECG wave form prior to amplification and is simultaneously transmitted as an FM modulated signal. In addition thereto, various alarm signals are transmitted as FM modulated signals with the pacer pulse.

7 Claims, 7 Drawing Figures

TELEMETRY SYSTEM AND METHOD FOR TRANSMISSION OF ECG SIGNALS WITH HEART PACER SIGNALS AND LOOSE LEAD DETECTION

BACKGROUND OF THE INVENTION

The present invention relates to the field of telemetric, biomedical devices, and, in particular, to telemetric systems for the tranmission of electrocardiographic (ECG) signals from a remotely located patient to a central receiving station.

DESCRIPTION OF PRIOR ART

Care of the critically ill patient has substantially improved over the last few years due largely to an increased ability to continuously monitor the patient's condition and to take immediate corrective action in order to anticipate distress or trauma and take a proactive action. Moreover, the continuous monitoring of a critical patient discloses symptoms which can be detected only through a period of prolonged and careful observation or by observation of short periods of dysfunction which unpredictably occur. In any case, the quality of care for the critical patient has become increasingly dependent upon a continuous ability to monitor such patients.

In order to effectuate critical care, wards have been set up within hospitals with personnel and equipment trained and adapted to monitor the vital signs of patients and to take appropriate responsive action. In the case of critical cardiac patients, such critical care includes the continuous monitoring of the ECG signals from each patient as well as the performance of an implanted pacemaker within the patient. The continuous monitoring of multiple patients at a central nursing station has thus become necessary and equipment has been devised in the prior art for providing a telemetric link between each patient in the ward and the central station. However, the nature of the pacemaker signal and the ECG signals is substantially different from each other. Typically, a pacer signal ranges in amplitude from a few millivolts to several hundred millivolts and may be of 50 microseconds to 2 milliseconds in duration. In contrast, the QRS complex of the human heart ranges in amplitude from 0.5 millivolts to 5 millivolts as detected at the patient's skin electrodes. Inherent bandwidth restrictions in the telemetry circuitry in the prior art have caused the transmission of the pacer pulse to become unacceptably distorted, mainly due to pulse stretching. It has become increasingly important in critical care patients to be able to accurately compare the actual pacer pulse to the heart performance as defined by the ECG signal. When the telemetry distorts the pacer pulse, it becomes virtually impossible at the receiving station to perform the necessary analysis to correlate the pacer's performance with the patient's heart.

In order to overcome this defect, prior art cardiac telemetric units have increased the bandwidth of the entire telemetry link in order to accommodate the pacer pulse. However, the results obtained by this solution have been unsatisfactory since an increase in bandwidth causes a severe degradation in the system's signal-to-noise ratio. Moreover, the greater the increase in bandwidth, the fewer the number of channels that can be accommodated on the assigned frequency band. Therefore, the number of patients who can be monitored by such a system has decreased in the face of increasing demand by physicians to make such critical care available to more and more patients within a hospital. Finally, increasing the bandwidth of the telemetry link substantially increases the cost of such a system, again in the face of mounting pressures to provide sophisticated in state-of-the-art medical care at the lowest possible cost.

Data provided into the telemetry link is ultimately derived through skin contacts placed on the patient which pick up both the pacer pulse and the ECG complexes. The quality of the signal, which in circumstances can be transmitted, is thus initially dependent upon and assumes a satisfactory skin contact with the patient. Quite commonly, and particularly over the course of time, one or more of the skin contact electrodes may loosen or its signal pick-up may otherwise degrade. This is generally denoted as a "loose lead" condition. In order to detect this loose lead condition, the prior art has devised circuitry whereby a high frequency signal, much higher than the ECG signals, is placed across the leads. As long as the lead contact is adequate, the high frequency signal is generally shunted through the patient and very little, if any, high frequency voltage would appear across the leads. However, upon the occurrence of a loose lead condition, the impedance between the leads increases and therefore the high frequency voltarge differential between the leads increases and becomes observable.

While this prior art method for detecting a loose lead condition is suitable in the case where the high frequency signal used for detecting the loose lead condition is several times higher than the frequency of the ECG complex, the prior art method becomes unacceptable and inadequate when it is also desired to monitor the pacer pulse. The frequency components of the pacer pulse are substantially greater than ECG signal and thus tend to interfere with the higher frequency loose lead signals. Thus, under the prior art methods, it has become impossible to both monitor a loose lead condition and to monitor the pacer pulses.

What is needed then is a cardiac telemetric system which is capable of transmitting the ECG wave forms and pacer pulses from a plurality of patients to a central station in such a manner that the loose lead condition can continue to be monitored without interference of either the detection of the pacer pulses or the ECG wave forms. What is described below is a system capable of providing this performance and capable of overcoming each of the above discussed deficiencies of the prior art systems.

BRIEF SUMMARY OF THE INVENTION

The present invention is a circuit for transmission of a physiological signal characterized by a first component signal within a first frequency band such as an ECG signal, and further characterized by a second signal within a second higher frequency band such as a pacer pulse. The circuit comprises electrode leads for receiving the physiological signal including the first and second component signals. A pulse limiter is coupled to the electrode leads. The pulse limiter generates a frequency modulated output signal indicative of the first component signal of the physiological signal. The pulse limiter is characterized by a limited slew rate wherein the second component signal and the physiological signal is substantially deleted from the output signal of the pulse limiter.

The invention also comprises a circuit for generating a signal indicative of faulty electrode contacts on a patient. The circuit comprises electrodes coupled to the patient which electrodes receive a physiological signal from the patient. Leads are coupled to the electrodes and communicate the physiological signals from the electrodes. A fixed frequency generator, typically operating at approximately 60 Hz generates a loose lead signal with a fixed frequency which is within the frequency spectrum of the physiological signal. The fixed frequency generator is coupled to the leads so that the loose lead signal generated by the fixed frequency generator is substantially shorted across the electrodes through the patient when the electrodes make suitable contact with the patient and when the loose lead signal tends to be open circuited across the leads when the electrodes fail to make suitable contact with the patient. The circuit of the invention then includes a subcircuit for detecting when the loose lead signal has achieved a predetermined magnitude across the leads which is indicative of inefficient electrode contact with the patient. The subcircuit discriminates the loose lead signal from the physiological signal and thus detects the loose lead condition without interference from reception in the subcircuit of the physiological signal from the patient. The circuit for detecting the loose lead signal comprises a transmitter and a receiver. The transmitter includes a pacer pulse limiter circuit which passes the loose lead signal and physiological signal. The physiological signal is characterized by a first component signal lying in the first frequency band and characterized by a second component signal within a second higher frequency band. The loose lead signal also lies within the first frequency band. The pacer pulse limiter circuit separates the second signal from the first signal and loose lead signal.

The invention also includes a method for monitoring and communicating a physiological signal which signal is characterized by a first portion within a first frequency bandwidth, such as an ECG signal, and is characterized by a second portion within a second higher frequency bandwidth, such as a pacer pulse. The method comprises the steps of receiving the physiological signal from the patient and separating the first and second portions of the physiological signal within the pacer pulse limiter, which generates a slew limited proportional pulse width output. The first and second portions of the physiological signal are then communicated as noninterfering components of an output signal. By reason of this combination of steps, a second portion of the physiological signal which is within the higher frequency bandwidth is received and communicated independently of the first portion of the physiological signal which is within the first frequency bandwidth. Thereby, independent signal handling and processing is both possible and practical. The step of separating is particularly characterized by slew limiting a proportional pulse width output generated in response to the physiological signal whereby the second portion within the second higher frequency bandwidth is effectively separated or removed from the output signal.

These and other embodiments of the present invention can be better understood by now turning to the following Figures wherein like elements are referenced by like numerals.

To better understand the invention and its illustrated embodiment in connection with the above schematics, turn now to the following detailed description.

DETAILED DESCRIPTION OF THE PREFERRED EMBODIMENT

The present invention is a cardiac telemetric system capable of transmitting pacer pulses and ECG wave forms from a plurality of critical care patients to a central receiving station while maintaining and testing for a loose lead condition on each patient. The invention allows such a system to be devised while maintaining an adequate signal-to-noise ratio, without reducing the number of available transmitting channels within an assigned frequency bandwidth and without substantially increasing the cost of manufacture of such a system.

Before turning to the detailed description as illustrated in the figures described above, consider first a general description of the invention's functions and attributes. The invention utilizes a novel method of transmitting both the pacer pulses and ECG wave forms by combining an FM-FM and direct FM signal on a single radio frequency carrier. The composite signal from the patient, which contains both the ECG wave form and the pacer pulse, is first amplified by a low gain differential amplifier. The slew rate limiting of the pacer pulse is proportional to its pulse width and then results in the deletion of most of the pacer pulse from the composite signal. Just enough of the pacer signal remains in the composite signal to indicate the polarity of the pacer pulse. The composite signal is then AC coupled and amplified through a high gain, narrow bandwidth amplifier. The ECG wave form is used to modulate a subcarrier oscillator. The subcarrier oscillator then frequency modulates the output of a radio frequency oscillator resulting in an FM-FM modulation which carries ECG information. A second output from the differential amplifier, upstream from the slew rate limiter of the pacer is provided for the pacer pulse channel. A filter is used to eliminate the ECG complex, and a detector and pulse shaper constructs a pulse flag of fixed amplitude, duration and polarity. The pulse flag is used to directly frequency modulate the radio frequency oscillator in the transmitter. Modulation of the radio frequency by the ECG complex and the pulse flag thus becomes mixed.

The direct FM and FM-FM signal is then transmitted to a receiving unit. The composite transmitted signal is separated at the receiver FM detector output. The pacer flag is recognized by the use of a peaked low pass filter followed by a peak detector, comparator and one shot multivibrator. The ECG component is demodulated using a phase-lock-loop demodulator which detects only the signal frequency modulating the subcarrier.

The loose lead condition is detected by the invention by using a low frequency AC voltage or current generator capacitively coupled to the patient's skin electrodes. An AC frequency detector is used after a low pass filter in the receiver to determine when a predetermined level of low frequency AC signal appears at the ECG leads. The level of this low frequency signal is proportional to the ECG patient lead resistance. The AC frequency is coupled to the electrodes through a resistance many orders of magnitude greater than the normal ECG lead resistance of the patient. Therefore, as long as good contact is maintained, no significant distortion of the ECG signal occurs. However when a loose lead contact begins to develop, the AC frequency will appear at the electrode and be detected at a preselected level.

Figure 1:
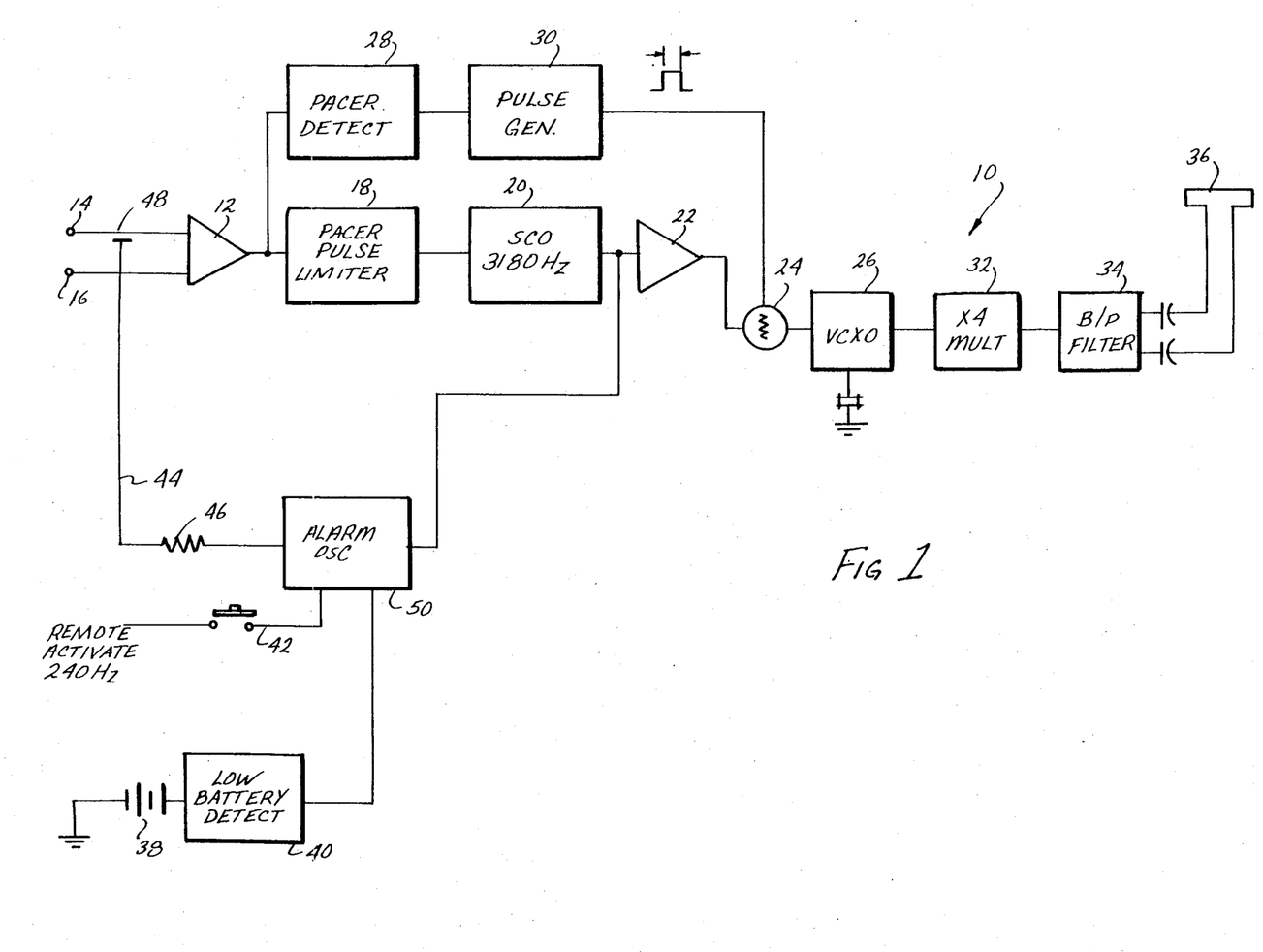
FIG. 1 is diagrammatic block diagram of a transmitter according to the invention.
Figure 2:
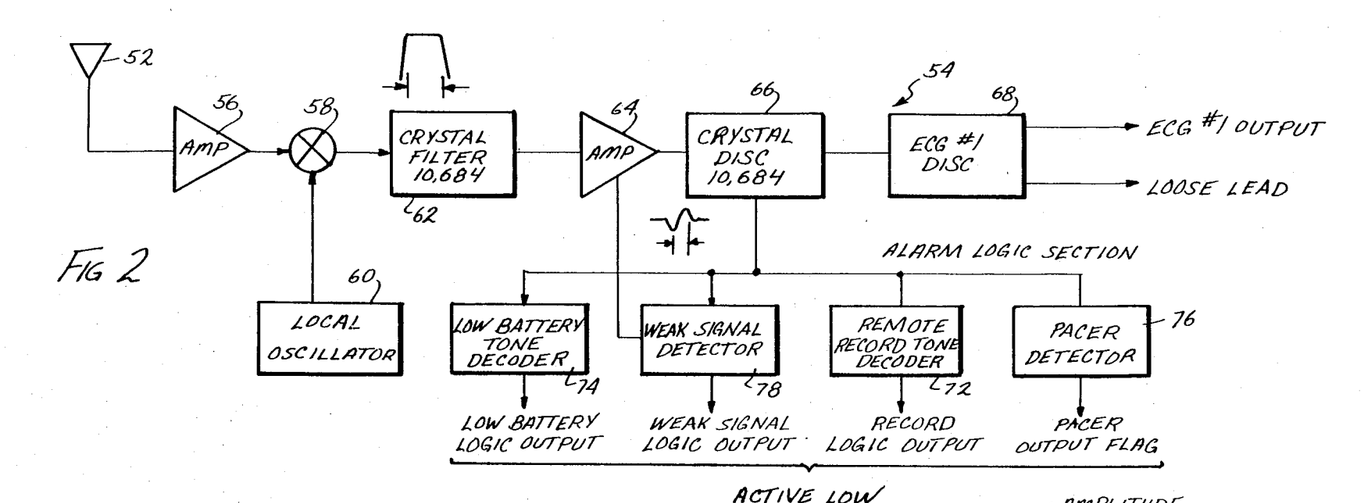
FIG. 2 is a diagrammatic block diagram of a receiver devised according to the invention.

The invention now having been generally described, turn now to the block diagram of FIG. 1 wherein a transmitter is diagrammatically depicted and to the block diagram of FIG. 2 wherein a patient receiver is diagrammatically depicted.

In FIG. 1, the transmitter, generally denoted by reference numeral 10, is comprised of a differential amplifier 12 having its inputs coupled to electrodes 14 and 16. Electrodes 14 and 16 are the ECG patient electrode, skin contacts which pick up the composite signal including the ECG wave form and the pacer pulse. The composite signal is generated as an output from differential amplifier 12 and coupled through a first path as an input to a pacer pulse limiter 18. Pulse limiter 18 attenuates the pulse, the pulse output amplitude which is proportional to the input signal width. By limiting, the slew rate of pacer pulse limiter 18, the high frequency components, corresponding to the pacer pulse within the composite signal provided at the input of limiter 18, are substantially attenuated and eliminated from the composite signal. Therefore, most of the information provided in the output of limiter 18 represents the ECG waveform and only enough of the low frequency contents of the pacer pulse is present in the output of limiter 18 to indicate the polarity of the pacer pulse. The output of limiter 18 is provided as an input to a subcarrier oscillator 20. In the illustrated embodiment, subcarrier oscillator 20 operates at a frequency of approximately 3180 Hz and generates an output which is frequency modulated by the output of limiter 18. The frequency modulated output of subcarrier oscillator 20 is then amplified through a high gain, narrow band amplifier 22 and summed at node 24. Node 24 is coupled to the input to a voltage controlled oscillator 26.

Meanwhile, the composite signal from the output of differential amplifier 12 is also provided as an input to a pacer detector 28. Thus, the composite signal is provided along a second path, the first path being provided as an input to limiter 18 and the second path provided as an input to pacer detector 28. The gain of amplifier 12 is set low enough to accommodate the full range of signal amplitude expected for the pacer pulse. Pacer detector 28, includes a 1 kilohertz bandpass filter which removes substantially all of the ECG waveform from the composite signal. The output of the bandpass filter included within detector 28 is amplified and provided as an input to a one-shot multivibrator 30. The output of multivibrator 30 is a pacer flag of a predefined amplitude, duration and polarity which is generated whenever a signal of sufficient amplitude, indicative of a pacer pulse is provided at its input. The output of multivibrator 30, the pacer flag, is then summed at node 24 with the frequency modulated subcarrier signal, both of which are simultaneously provided as inputs to voltage controlled oscillator (VCO) 26. Voltage oscillator 26 is a conventional VCO with a crystal controlled output of approximately 50 megahertz. The output of VCO 26 is quadrupled by multiplier 32 to approximately 200 megahertz. The output of multiplier 32 is coupled through a conventional band pass filter 34 and then capacitively coupled to a radio frequency antenna 36.

Return now to FIG. 1. The system's battery voltage, generated by a conventional battery 38, is monitored by a battery detection circuitry 40. Battery detection circuitry 40 will generate a 300 hertz signal whenever the voltage battery 38 falls below a preselected magnitude. A remote switch 42, accessible to the patient, is used to generate a 240 hertz signal which can be used either as an event marker by the patient, a nurse call button, and a calibration signal. Finally, the low frequency loose lead signal is capacitively coupled to electrodes 14 and 16 through proximity capacitor 48 presenting a very high impedance to provide a low frequency AC signal indicative of a loose lead connection. Wire 44 is coupled to lead 14, for example, through a low capacitence AC coupling 48, which may in fact be the simple juxtaposition of wire 44 disposed and maintained in the proximity of electrode wire to electrode 14. These three signals, the 300 hertz low battery signal from detector 40, the 240 hertz remotely activated signal coupled through switch 42 are each provided as outputs from an alarm oscillator 50. The alarm oscillator 50 is coupled to the input of band pass filter 22. Thus, a low battery detector signal, and the remote activation signal are additionally provided to node 24 and are used to directly frequency modulate the transmitted RF signal. It should be noted that each of these signals are near the frequency bandwidth of the ECG wave form and are superimposed low frequency signal modulation, whereas ECG wave forms are carried on the 3,180 hertz subcarrier frequency which is used to FM-FM modulate the radio signal. Therefore, the interference in the transmitted signal between these alarm signals and the ECG wave form is insignificant.

Before discussing other features of the transmitter 10 in FIG. 1, turn momentarily to the schematic diagram of FIG. 2 wherein a receiver of the invention is illustrated. The transmitted radio frequency signal from transmitter 10 in FIG. 1 is received by an antenna generally denoted by the reference numeral 52 in FIG. 2. The radio signal is amplified by a conventional radio frequency amplifier 56 and then provided as an input to a conventional mixer 58. A local crystal controlled oscillator 60 is provided as the other input to mixer 58 to hetrodyne the RF signal down to approximately 10.7 MHZ. The output of mixer 50 is then provided to a conventional crystal filter 6 which in turn passes the intermediate frequency of approximately 10.7 Mhz. The intermediate radio frequency is amplified by IF amplifier 64 whose output in turn is coupled to an input of a conventional crystal controlled discriminator 66 operating at the intermediate frequency of 10.7 Mhz. The output of crystal discriminator 66 thus includes the pacer pulse, the ECG waveform, and various alarm signals discussed below, including the loose lead alarm signal. At this point, at the output of crystal discriminator 66, the alarm signals are demodulated while the loose lead alarm signal and ECG waveform continue as FM modulation of the 3180 hertz subcarrier. The alarm signals are split from the subcarrier by circuitry described in greater detail below in connection with FIG. 7, which is symbolically included within crystal discriminator 66 in schematic FIG. 2, while the subcarrier signal is coupled to a second subcarrier demodulator 68 which performs a second FM demodulation to strip off the ECG waveform and loose lead signal from the subcarrier. These two signals in turn are separated by circuitry included in ECG discriminator 68 and described below in greater detail in connection with FIG. 7. These signals are later processed to detect the loose lead condition and to present the ECG signals available at the output of discriminator 68 as an analog signal. The pacer signal is reconstructed from output 70 of discriminator 66 in a pacer detector circuit 76.

Meanwhile, the fully demodulated alarm signals are generated at output 70 of discriminator 66 and provided and separated at the inputs of respective detector circuitry as depicted in FIG. 2, labelled generally as alarm logic section 71. The transmission and reception of the pacer pulse signal and ECG waveform have now been traced through the circuitry of FIGS. 1 and 2. However, as mentioned above, in addition to these signals, there are a plurality of alarm signals such as the loose lead signal, remote call, weak RF alarm and low battery alarm signals. First consider how each of these alarm signals are generated in the transmitter and then detected in the receiver.

Consider now the reception and detection of these alarm signals in FIG. 2. The low battery 300 hertz signaal and the remote call 240 hertz signal are separated in FIG. 2 from the other alarm signals by an alarm low pass filter described below in greater detail in FIG. 7 and separately detected in FIG. 2, in tone detector 72 in the case of the remote record 240 hertz signal, and tone decoder 74 in the case of the low battery 300 hertz signal. The pacer pulse is similarly separated by an appropriate low pass filter and detected by a pacer flag detector. The triggering of detector 76 causes then reconstruction of the pacer flag by a one-shot multivibrator, all of which is symbolically included and denoted as pacer detector 76. Finally, an output is taken directly from RF amplifier 64 simply to detect whether or not an RF signal, whether it be modulated or not, is being transmitted and received. In the event that an RF signal is not being received, a weak signal detector 78 coupled to RF amplifier 64 is activated to produce an appropriate alarm.

The above description in connection with FIGS. 1 and 2 has broadly described the transmitter and receiver and has assumed throughout the discussion that a single pair of leads from a single patient was monitored. It is clearly within the scope of the invention and is contemplated within the preferred embodiment that each patient's transmitter and receive channel will be arranged and configured to carry a plurality of lead pairs. Generally, two pairings of three electrodes is used in cardiac monitoring. In that case, in FIG. 1 the ECG amplifier broadly comprising differential amplifier 12, limiter 18, subcarrier oscillator and band pass filter 22 is duplicated for the second pair of leads. The remaining portions of the circuitry as illustrated in FIG. 1 are shared in common between the two electrode pairs. In addition, it is only necessary for pacer detector 28 to pick up the pacer pulse from only one of the pair of electrodes. Therefore, the transmitter in FIG. 1 can be easily expanded to include two or more additional electrode pairs by providing a differential ampliifier, limiter, subcarrier oscillator and bandpass filter in parallel to those illustrated, which circuits would then operate at a distinguishable subcarrier frequency. Each of the channels are summed at node 24 and transmitted in common modulation through the remaining stages of the FM transmitter. Similarly, in the receiver, a second ECG discriminator similar to discriminator 68 is provided for the second pair of electrodes, the information from which is transmitted at the second subcarrier frequency. FIG. 2 is thus modified by simply providing a second ECG discriminator in parallel to discriminator 68.

Figure 3:
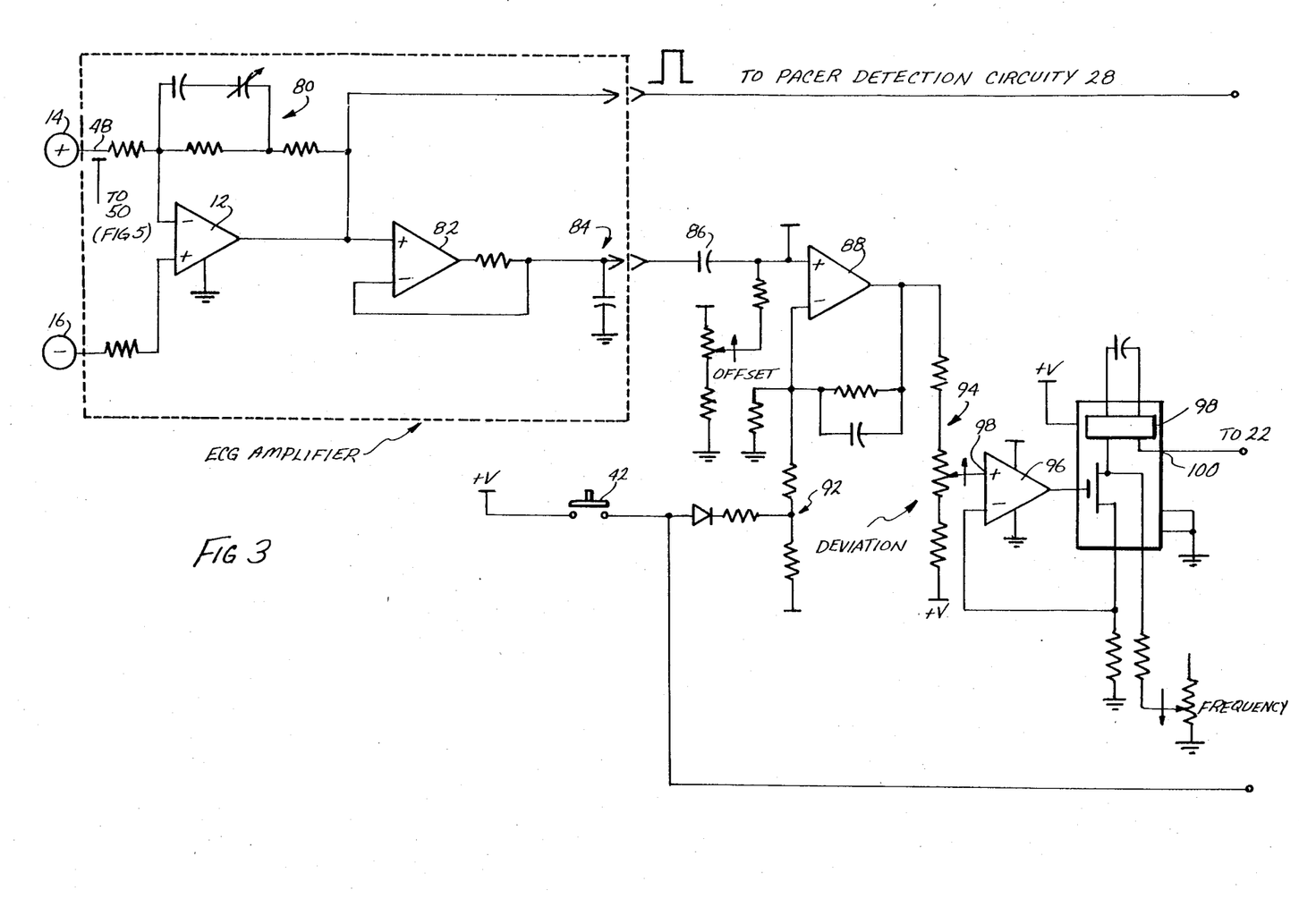
FIG. 3 is a more detailed schematic of a portion of the transmitter shown in FIG. 1.

Turn now to FIG. 3 wherein a more detailed schematic of the transmitter is illustrated. Patient leads 14 and 16 are shown as resistively coupled to inputs of a differential amplifier 12. The 60 hertz loose lead signal, generated by means described below, is coupled to input 14 through a loose capacitive coupling 48. The ECG signal, loose lead 60 hertz signal, and pacer signal are thus provided across the inputs of differential amplifier 12. The signal from electrode 14 is filtered by passive RC filter, generally denoted by reference numeral 80, and as will be discussed below, is provided to the input of a pacer detection circuitry 28.

Meanwhile, the output of differential amplifier 12 is coupled to one of the inputs of a slew limiter 82. The output of slew limiter 82 is a signal having a pulse amplitude proportional to the pulse width of differential output 12. The slew rate of amplifier 82 is such that it is unable to respond to the higher frequency components which are generally indicative of the pacer pulse, but is able to respond to the 60 hertz loose lead signal and the low frequency ECG signals. The output of amplifier 82 is capacitively coupled through capacitor 86 to a buffer 88. In addition to signal conditioning, buffer 88 is an active half-hertz filter which removes any very low frequency drift. A calibration remote call signal is also coupled from a 6 volt supply through push button switch 42 and a passive resistive network generally denoted by reference numeral 92, which is coupled to one of the inputs of buffer 88 to cause a calibration signal to be coupled to its output. The output of isolator 88 is coupled through a resistive network, generally denoted by reference numeral 94, to the input of a subcarrier oscillator deviation circuit 96. In the preferred embodiment, circuit 96 generates an oscillatory output proportional to the voltage at its input 98 of approximately 60 hertz per millivolt. The output of oscillator 96 is coupled to a subcarrier oscillator chip 98, such as type MC-14046 PCB, which generates a frequency modulated subcarrier oscillator of approximately 3180 hertz. Therefore, the loose lead signal and ECG signals deviate at the output 100 of chip 98 at the subcarrier oscillator frequency of 3180 hertz. The high frequency pacer pulse signal is separated by a slew limitation of slew limiter/amplifier 82. Thus, the circuitry comprised of circuits 82 and 88 and associated components of FIG. 3 generally correspond to pacer pulse limiter 18 of FIG. 1, while subcarrier oscillator 20 of FIG. 1 corresponds to circuitry 96 and 98 of FIG. 3.

Figures 4, 5:
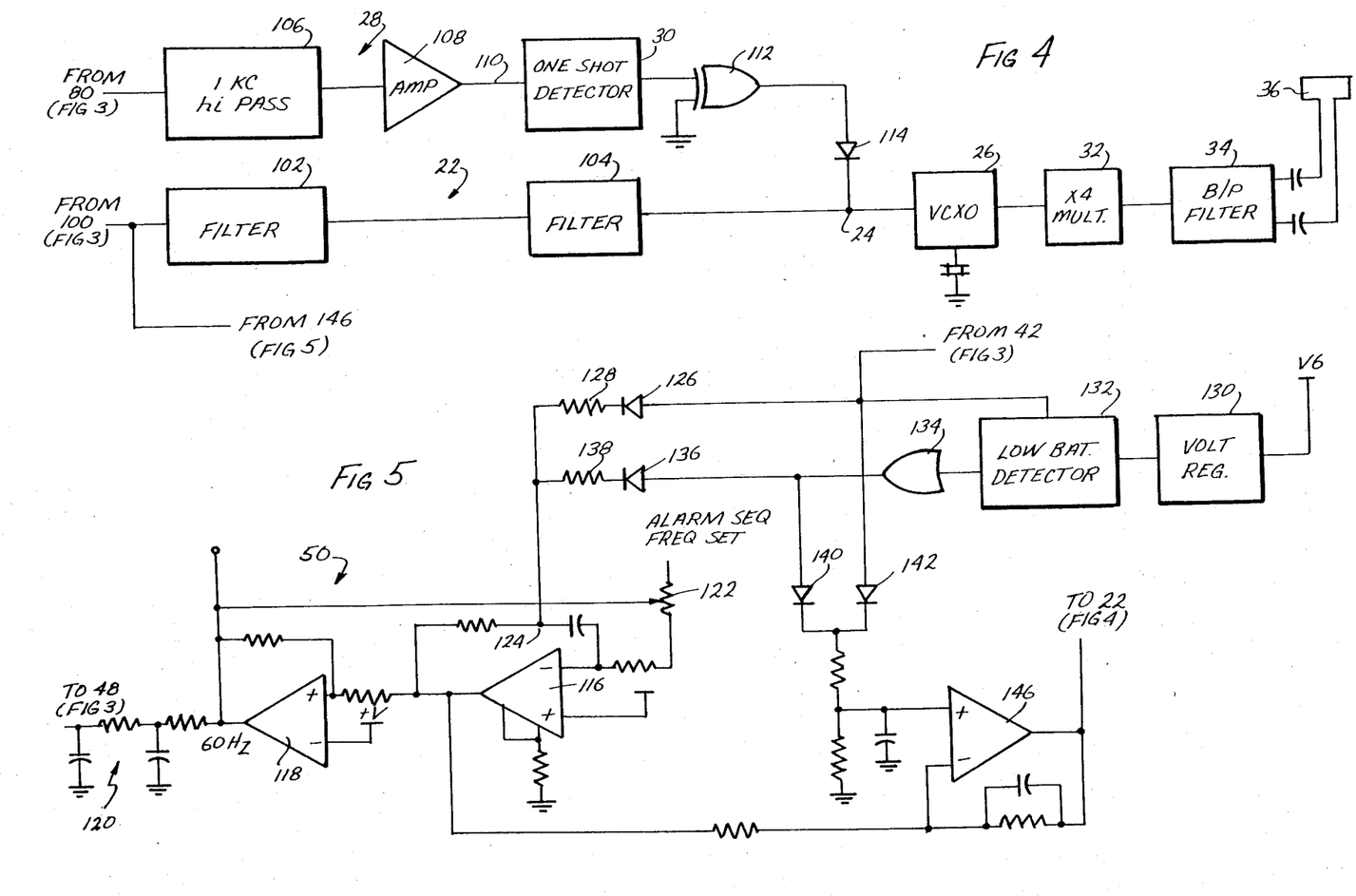
FIG. 4 is a block diagram of the remaining portion of the transmitter shown in FIG. 1.
FIG. 5 is a somewhat more detailed schematic of an alarm oscillator included as part of the transmitter illustrated in FIG. 1.

Turn now to FIG. 4 wherein the FM signal from output 100 of chip 98 is coupled through a summation filter generally denoted by reference numeral 102 and 104. These circuits serve to filter out any signals extraneous to the 3180 hertz modulated subcarrier.

Meanwhile, the pacer pulse from the output of filter 80 in FIG. 3 is coupled to a one kilohertz high pass filter generally denoted by reference numeral 106 in FIG. 4. The lower frequencies associated with the ECG signals and loose lead signals are thus attenuated by high pass filter 106, which generates a pulse indicative of the pacer pulse. The output of high pass filter 106 in turn is amplified by amplifier 108 and the signal generally conditioned to be provided as an input to a one-shot multivibrator, generally denoted by reference numeral 30. The output of one-shot multivibrator 30 is a 40 millisecond square wave pulse which is generated whenever a signal of sufficient magnitude is coupled to its input 110. The output of one-shot 30 is capacitively coupled to one input to a gate 112. Gate 112 simply provides for signal buffering and conditioning. The output of gate 112 is thus a 1 millisecond square wave corresponding to the 40 millisecond square wave of the output of one-shot 30. The output of gate 112 is thus coupled through a diode 114 to node 24. As described in connection with FIG. 1, node 24 is also coupled to the output of band pass filter 22. The signal at the output of band pass filter 22 is the filtered FM modulated ECG and loose lead signal ultimately originating from differential amplifier 12. The signal at node 24, consisting of the algebraic addition of the pacer pulse signal coupled through diode 114 and the filtered FM modulated 3180 hertz signal from bandpass filter 22, is then coupled through a conventional voltage controlled oscillator 26, multiplier 32, bandpass filter 34 and RF antenna 36 as described and depicted in connection with FIG. 1. The transmission in the preferred embodiment is approximately 200 Mhz and frequency modulates signal corresponding to the pacer pulse and an FM-FM signal corresponding to the loose lead and ECG signal.

Turn to FIG. 5 which shows the loose lead, low battery remote activation subcarrier oscillator. The alarm oscillator 50 generally shown in FIG. 5 is comprised of a two stage oscillator including first stage 116 and second stage 118. Together circuits 116 and 118 including associated passive circuitry as shown in FIG. 5 constitute a selectively controlled alarm oscillator. Normally, the output of second stage 118 is a 60 hertz signal. This is the loose lead signal which is coupled through a passive 60 hertz lowpass filter generally denoted by reference numeral 120, and then loosely capacitively coupled through a juxtapositioned wire symbolically denoted as capacitor 48 in FIGS. 1 and 3. The 60 hertz output from second stage 118 is typically set through a variable resistor 122 in the feedback loop between first and second stages 116 and 118. However, by varying the voltage applied to node 124 in the feedback loop of first stage 116, the output of the alarm oscillator 50 and in particular, second stage 118 can be varied depending on the voltage applied. For example, a 6 volt signal coupled through push button 42 as shown in FIG. 3 is coupled through diode 126 and resistor 128 to node 124 to inject a voltage which will cause alarm oscillator 50 to generate a 240 hertz output signal. The signal frequency chosen is arbitrary and many other equivalent frequencies could have been equivalently substituted. However, 240 hertz is the frequency selected in the preferred embodiment.

Similarly, the battery which powers the patient unit is coupled to a conventional voltage regulator diagrammatically depicted by reference numeral 130 in FIG. 5, whose output in turn, is coupled to a low battery detection circuit generally denoted rby reference numeral 132. When the output of regulator 130, following the output of the battery, reaches a predetermined voltage, detection circuit 132 is turned on and coupled through gate 134. The output of gate 134 in turn is coupled to a protection diode 136 and resistor 138 to node 124 in feedback loop of first stage 116. Due to the resistive values and voltages chosen, a second distinguishable voltage will be impressed upon node 124 in alarm oscillator 50, and in particular, the output of second stage 118 will be caused to generate a 300 hertz signal. Thus, the 300 hertz signal in the preferred embodiment is indicative of a low battery condition. Neither one of these signals are able to pass through lowpass filter 120, but both of them are coupled from the output of first stage 116 to one input of a driver circuit 146. Driver circuit 146, in turn is activated by the voltage from push button 42 or gate 134 through diode 142 and 140, respectively, and a resistive network, generally denoted by reference numeral 144, which is coupled to the other input of driver 146. Driver 146 thus being enabled then buffers and amplifies the 240 or 300 hertz signal from the alarm oscillator and provides that signal and its output to the input of bandpass filter 102. From the input of bandpass filter 102, the 240 hertz remote call signal or the 300 hertz battery signal is treated in an identical manner to the FM modulated signal from output 100 of chip 98. Thus, when either of these signals is active they ultimately are FM modulated along with the pacer pulse in the 200 Mhz signal broadcast through antenna 36.

The transmission circuitry now having been described, turn now to the detailed schematics of the receiver which has previously been generally described in connection with the block diagram of FIG. 2. Turn to FIG. 6. The RF signal, generated by the circuitry described above, is received by antenna 52 shown in FIG. 2 and is coupled to a conventional RF amplifier 56. The receive signal in the preferred embodiment is in the range of 174 to 216 megahertz. The output of RF amplifier 56 in turn is coupled to a conventional mixer 58 where it is mixed with the output signal of a crystal controlled local oscillator 60. The output of mixer 58 is coupled through a conventional 8 pole 20 kilohertz bandpass filter 62 tuned to 10.684 megahertz. The intermediate frequency of 8 pole filter 62 in turn is coupled to the input of a conventional intermediate frequency discriminator 67, such as type CA 3189E. Discriminator 67 is a modular chip, which includes an intermediate frequency amplifier shown as amplifier 64 in FIG. 2, which in turn is coupled to a level detector and tuning meter circuit all included in circuit 67. The output of the tuning meter circuit within the modular circuit 67 is indicative of the strength of the RF signal being received. This voltage is compared against an arbitrarily adjusted reference voltage from resistive network 150 within a detector amplifier 152. The output of amplifier 152 is then coupled to an RF detector described in greater detail below.

Discriminator circuit 67 demodulates the intermediate frequency thereby producing at its output the FM modulated 3180 kilohertz subcarrier frequency, the pacer pulse signal, low battery and remote call signal. The loose lead and ECG signal remain FM modulated on a 3180 kilohertz subcarrier. The output of discriminator 67 is thus coupled through a passive filter network, generally denoted by reference numeral 154, to the input conventional buffer amplifier 156. The output of buffer amplifier 156, in turn, is coupled through the input of a conventional 5 kilohertz low pass filter, generally denoted by reference numeral 158 in FIG. 7. The high frequency pacer pulse is thus effectively removed by low pass filter 158. The output of low pass filter 158 is coupled to the input of a conventional active high pass 1.3 kilohertz filter 160. Filter 160 thus serves to separate the 300 and 240 hertz alarm signals, but still allows the 3180 kilohertz signal to easily pass through. Filters 158 and 160 thus form a frequency window through which only the frequency modulated 3180 kilohertz signal, bearing the ECG and loose lead information can pass. The output of high pass filter 160 is then coupled to a conventional subcarrier phase-lock-loop demodulator, such as type XR2211, denoted by reference numeral 162. The output of demodulator 162 is thus a signal representative of the ECG and loose lead signals. Superhetrodyned harmonics or high frequency signals are then removed by coupling the output of demodulator 162 to a conventional low pass filter 164. The output of low pass filter 164 in turn is then filtered again by a conventional active low pass filter 166 which will remove signal at or above 110 Hz. The output of low pass filter 166 is coupled to a conventional output buffer 168 which conditions the ECG signal and presents it as an analog output suitable for CRT or chart display.

Figure 7:
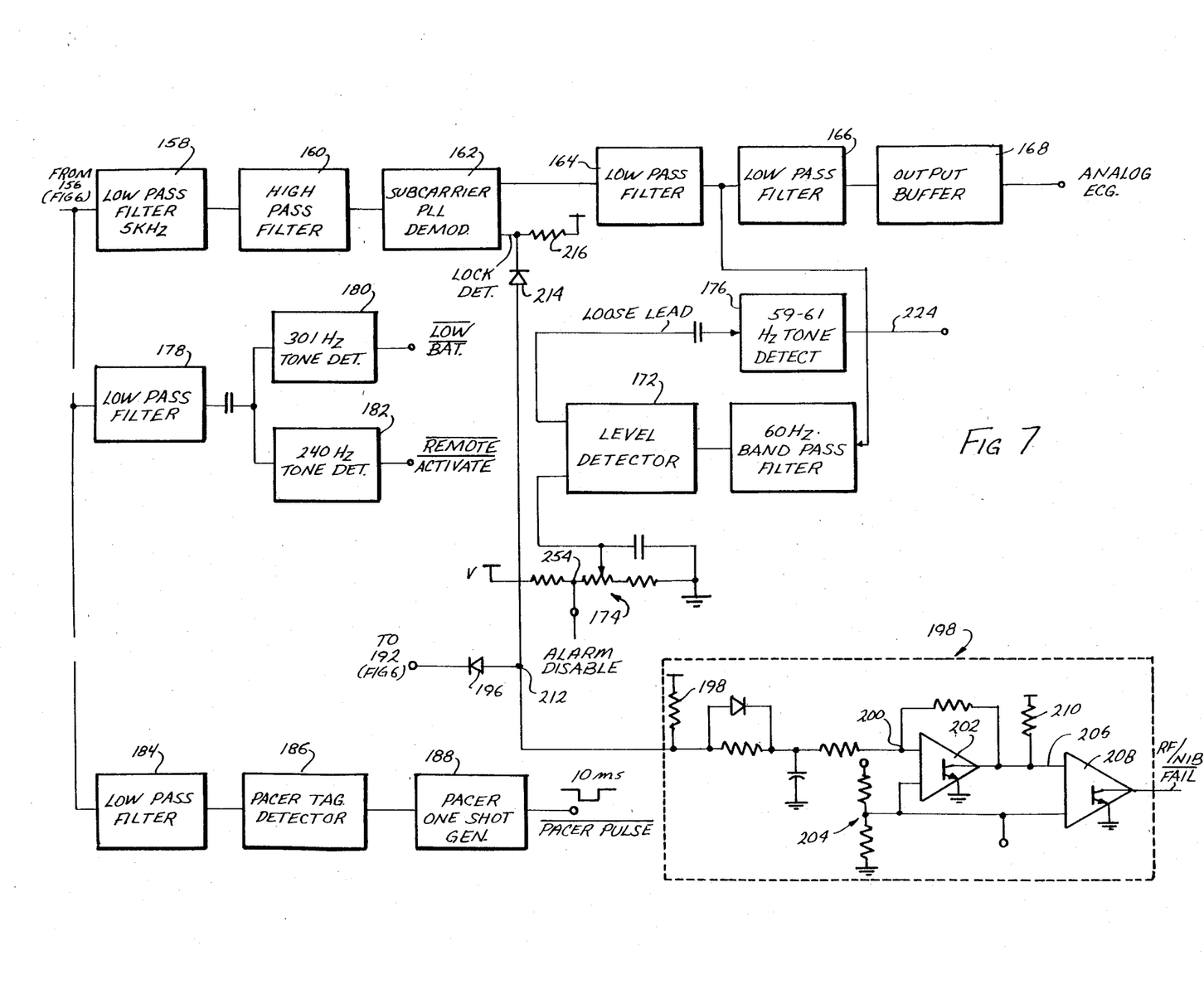
FIG. 7 is a block diagram of the remaining portion of the receiver illustrated in FIG. 2.

Meanwhile, the output of low pass filter 164 is also coupled to a conventional 55 hertz bandpass filter 170 which filters out the ECG component and passes the loose lead signal. The output of bandpass filter 170 in turn is coupled to a conventional voltage level detector 172, which measures the transmitted 60 hertz signal indicative of a loose and compares it against a reference voltage, arbitrarily selected from resistive network generally denoted by reference numeral 174. If a sufficient magnitude loose lead signal is detected, loose lead detector 172 generates a 60 hertz output which is coupled to the input of a conventional tone detector generally denoted by reference numeral 176. Tone detector 176 is a modular circuit, such as type LM 567N which generate an active low signal in response to detecting a 60 hertz signal. Tone detector 176 in the preferred embodiment includes a pair of parallel tone detectors, one set for 58 hertz and the other set for 60 hertz in order to reliably detect the loose lead signal whose frequency as received may vary by a few percent. The output of tone detector 176 may be used as an alarm disable signal as well as an active low, lead-off signal to disable the active low low-battery, remote activate, and pacer flag outputs as well.

Consider the output of buffer amplifier 156, in addition to being coupled to a low pass filter 158 to ultimately generate the ECG analog signal, is also coupled to an alarm low pass filter 178 in FIG. 7 which separates out the higher frequency components corresponding to the pacer pulse. The 300 hertz signal and 240 hertz remote activation signal are passed by a conventional active low pass filter 178 which has its output capacitively coupled to a modular, low battery tone detector 180 and a modular remote activate tone detector 182. Each of these circuits are modular circuits for detecting a specified tone frequency, such as modular types LM 567N, and are respectively tuned to 300 hertz and 240 hertz. The active low output signal which is generated is coupled to provide the low battery and remote activate output signals.

The output of buffer amplifier 156 is also coupled to a conventional low pass filter 184 in FIG. 7. Low pass filter 184 is set to pass the frequency components of the pacer pulse or lower and to filter out all higher harmonics and frequencies. Filter 184 has its output and turn coupled to a pacer tag detector which monitors the output of filter 184 for a level of a predetermined magnitude. Once a signal with a magnitude of the pacer pulse is detected, detector 186 generates an active low output which in turn is coupled to a conventional one shot generator 188. Generator 188 generates an active low, 10 millisecond, square wave pulse thereby reconstructing the pacer pulse. This pulse is subsequently made available as an output signal.

Figure 6:
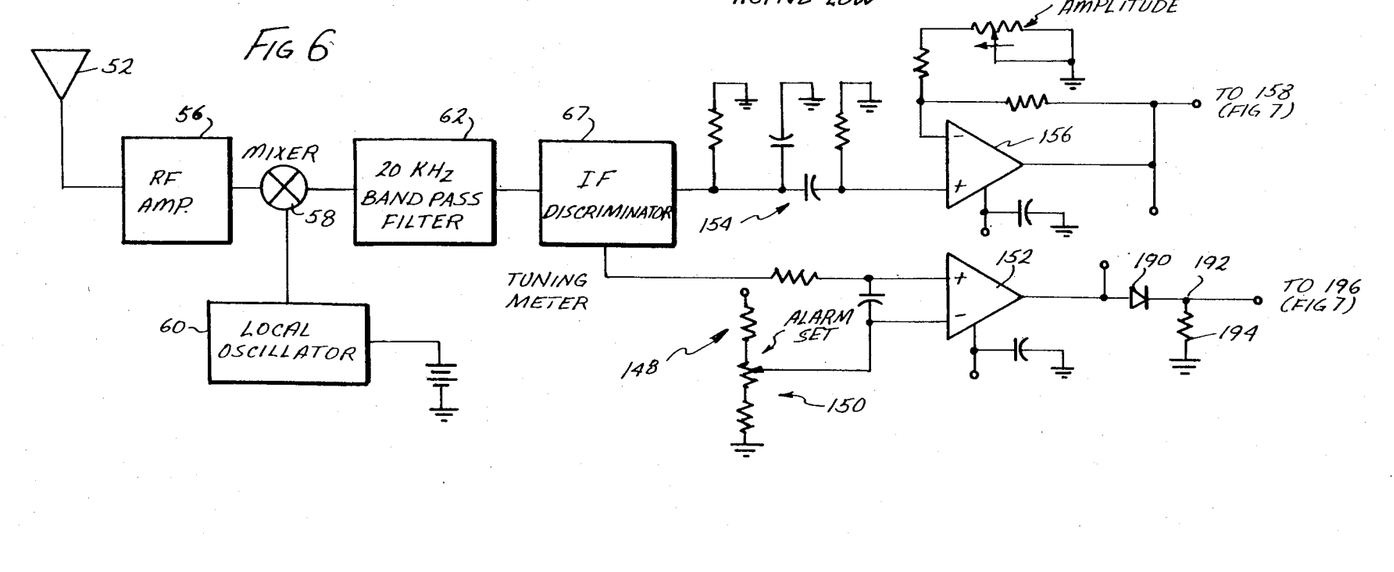
FIG. 6 is a somewhat more detailed block diagram and schematic of a portion of the receiver of the invention illustrated in FIG. 2.

However before turning to the available output signals, redirect your attention again to the RF detection signal as shown and described in connection with circuitry 148 of FIG. 6. The output of detector 152 is coupled through a diode 190 to a node 192 which in turn is coupled through resistor 194 to ground. Node 192 is also coupled through a diode 196 in FIG. 7 to a RF/NIB detect circuitry, generally denoted by reference numeral 198. Detection circuitry 198 generates as its output an RF/NIB fail active low signal which is provided as a system output signal to indicate either a weak RF signal or failure to remain in the band of phase lock loop demodulation. A pull-up resistor 198 maintains node 200 at or near the supply potential. Node 200 is coupled to a level detector 202 whose other input is maintained at a reference by a passive resistive network 204. The output of level detector 202 is active low and thus is generally in a low state, thereby maintaining the potential at node 206 low. Node 206 is coupled to one input of a level detector 208 whose other input is similarly coupled to the reference voltage from voltage divider 204. As a result, the output of detector 208, which is also active low remains high, that is the RF/NIB fall signal, remains inactive high.

However, when an insufficient RF signal is received, diode 190 (FIG. 6) will be reversed biased and caused to not conduct. Node 192 will thus be pulled low to a point determined by the relative ratios of resistor 194 (FIG. 6) and 198 (FIG. 7). In the preferred embodiment, resistor 194 is 470 ohms while resistor 198 is 10 Megohms, thus the potential at node 200 is near ground. This causes detector 202 to cease conducting thereby allowing the voltage supply to pull node 206 high through resistor 210. This, in turn, causes detector 208 to conduct and its output to thus be driven active low.

Node 200 is also coupled to subcarrier phase lock loop demodulator 162. More specifically, node 212 is coupled through diode 214 to the lock detection output of modular circuit 162. Normally, diode 214 is reversed biased through the voltage supply through resistor 216. However, when the lock detection circuit goes active low diode 214 becomes forward biased through the voltage supply through resistor 198. This causes node 212 to go toward ground. Again, as the normally high state at node 200 is driven to ground, the output of detector 208 goes active low. This then indicates either a failure to receive the RF signal or to modulate it in the first stage, or a failure to make an adequate second demodulation in circuit 162.

Many modifications and alterations may be made by those having ordinary skill in the art without departing from the spirit and scope of the invention. For example, although the detailed schematic has been described in terms of a single electrode pair, it is entirely within the scope of the invention that multiple electrode pairs can be accommodated by duplicating the appropriate portions of the circuitry,. More specifically in the receiving unit, subcarrier phase-lock-loop demodulator 162, low pass filter 164, band pass filter 170 and level detector 172 rwould be duplicated for the second pair of leads and would operate at a distinguishable subcarrier frequency. Similarly, low pass filter 166 and output buffer 168 would be duplicated for the ECG output of the second pair of leads. In addition thereto, what has been decribed above, is a transmitter and receiver for a single patient. Clearly, multiple patients can be multiplexed by extending the teachings of the above description in a manner well known to the art.

Therefore, the illustrated embodiment, which has been described, has been set forth only for the purposes of example and clarity and should not be taken as limiting the invention as rdefined by the following claims.

We claim:

1. A circuit for transmission of a physiological signal characterized by an ECG signal within a second higher frequency band, said circuit comprising:
   lead means for receiving said physiological signal including said ECG and pacer signals;
   separation composition means coupled to said lead means, said separation/composition means for generating a frequency modulated output signal indicative of said ECG signal of said physiological signal, said separation/composition means characterized by a limited slew rate wherein said pacer signal of said physiological signal is substantially deleted from said modulated output signal,
   pacer detection means coupled to said lead means for detecting said pacer signal included within said physiological signal, wherein said pacer detection means generates and output signal indicative of the presence or absence of said pacer signal within said physiological signal,
   pulse generator coupled to said pacer detection means and responsive to said output signal from said pacer detection means, said pulse generator is for generating a predetermined pulse flag signal, said pulse flag signal and said modulated output signal of said separation/composition means being summed within said separation/composition means to provide a composite signal characterized by said flag signal and a frequency modulated output signal carried on a first predetermined subcarrier frequency indicative of said ECG signal of said physiological signal,
   FM transmission means coupled to said separation/composition means for receiving said composite signal, said FM transmission means for frequency modulating said composite signal and transmitting said frequency modulated composite signal, whereby said FM transmission means transmits an FM modulated output signal indicative of said pacer signal of said physiological signal and an FM/FM modulated signal indicative of said ECG signal of said physiological signal
   whereby said ECG and pacer signals within said physiological signal are separated and thereafter may be further processed and transmitted.

2. The circuit of claim 1 further comprising an alarm oscillator means coupled to said lead means, said alarm oscillator means for generating a loose lead signal across said lead means, said loose lead signal having a frequency within said frequency band characteristic of said ECG signal of said physiological signal, said loose lead signal normally being applied across a low impedance of said lead means unless said lead means assumes a defective status whereupon said loose lead signal is applied across a higher impedance of said lead means, said loose lead signal being coupled through said lead means to said separation/composition means and frequency modulated on said first predetermined subcarrier with said ECG signal of said physiological signal,
   wherein said alarm oscillator means further generates a plurality of selectively activated alarm signals, said alarm oscillator means and said alarm signals being coupled to said separation/composition means, whereby said plurality of alarm signals is also frequency modulated on said second subcarrier with said composite signal.

3. The circuit of claim 1 further comprising receiver means for receiving said transmitted signal from said transmission means coupled to said receiver means, and means for demodulating said transmitted signal to generate a receiver output signal indicative of said ECG of said physiological signal and a distinct receiver output signal indicative of said pacer signal of said physiological signal.

4. The circuit of claim 3 wherein said receiver means comprises means for generating a second receiver output signal indicative of said loose lead signal, said loose lead signal being demodulated from said first subcarrier.

5. The circuit of claim 4 wherein said receiver means comprises means for generating a reconstructed flag signal demodulated from said second subcarrier and indicative of said pacer signal of said physiological signal.

6. A method of monitoring and communicating a physiological signal characterized by a first portion within a first frequency bandwidth and characterized by a second portion within a second higher frequency bandwidth comprising the steps of:
   receiving said physiological signal from a patient;
   separating said first and second portions of said physiological signal; and
   communicating said first and second portions of said physiological signal in distinct modulation formats as non-interfering components of an output signal; whereby said second portion of said signal within said second higher frequency bandwidth is received and communicated independently of said first portion of said physiological signal within said first frequency thereby permitting independent signal handling and processing thereof.

7. The method of claim 6 further comprising the steps of:
   frequency modulating said first portion of said physiological signal on a first predetermined subcarrier frequency;
   summing said frequency modulated first portion of said physiological signal with said separated second portion; and
   frequency modulating said summed, frequency modulated first portion and separated second portion of said physiological signal on a predetermined subcarrier, to provide an FM/FM output signal corresponding to said first portion of said physiological signal and an FM modulated component of said output signal corresponding to said second portion of said physiological signal.

* * * * *